US009801558B2

(12) United States Patent
Morren

(10) Patent No.: US 9,801,558 B2
(45) Date of Patent: Oct. 31, 2017

(54) DETECTION AND MONITORING OF ABDOMINAL AORTIC ANEURYSM

(75) Inventor: Geert Gui Georges Morren, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 188 days.

(21) Appl. No.: 13/811,297

(22) PCT Filed: Jul. 14, 2011

(86) PCT No.: PCT/IB2011/053146
§ 371 (c)(1),
(2), (4) Date: Jan. 21, 2013

(87) PCT Pub. No.: WO2012/011029
PCT Pub. Date: Jan. 26, 2012

(65) Prior Publication Data
US 2013/0116576 A1 May 9, 2013

(30) Foreign Application Priority Data
Jul. 21, 2010 (EP) .................................. 10170325

(51) Int. Cl.
*A61B 5/02* (2006.01)
*A61B 5/0295* (2006.01)
(Continued)

(52) U.S. Cl.
CPC ........ *A61B 5/0295* (2013.01); *A61B 5/02014* (2013.01); *A61B 5/0261* (2013.01);
(Continued)

(58) Field of Classification Search
None
See application file for complete search history.

(56) References Cited

U.S. PATENT DOCUMENTS 3,704,706 A * 12/1972 Herczfeld ............... A61B 5/024
356/41
4,356,486 A * 10/1982 Mount ................. A61B 5/0002
128/903
(Continued)

FOREIGN PATENT DOCUMENTS

| RU | 2199944 C2 | 3/2003 |
| WO | WO2007097702 A1 | 8/2007 |
| WO | WO2007107904 A2 | 9/2007 |

OTHER PUBLICATIONS

Kleinstreuer et al. "Analysis and computer program for rupture-risk prediction of abdominal aortic aneurysms," BioMedical Engineering OnLine, 5:19, 2006.*

(Continued)

Primary Examiner — Amelie R Gillman

(57) ABSTRACT

Ruptured Abdominal Aortic Aneurysms (AAA) cause a large number of deaths annually. Ruptures occur even in people who are already diagnosed with AAA and are being monitored. The reason is that the interval between tests is too long because of the need to visit a pathological facility with imaging equipment. It is preferable to estimate the progress of AAA frequently, once detected, in a non-invasive manner, preferably at the subject's home, without the need for the subject to visit a pathological facility. A device is disclosed for detecting a state of a vascular pathology of a subject, comprising a sensor signal unit (103) for providing a signal representative of a blood volume in a body part of a subject, a comparator (107) for comparing the sensor signal with a reference signal, and a user interface (109) for conveying a result based on the comparison to a user of the device.

5 Claims, 3 Drawing Sheets

(51) Int. Cl.
*A61B 5/024* (2006.01)
*A61B 5/026* (2006.01)
*A61B 5/0285* (2006.01)
*A61B 5/04* (2006.01)
*A61B 5/0402* (2006.01)
*A61B 5/00* (2006.01)

(52) U.S. Cl.
CPC ........ *A61B 5/0285* (2013.01); *A61B 5/02416* (2013.01); *A61B 5/0402* (2013.01); *A61B 5/04012* (2013.01); *A61B 5/7246* (2013.01); *A61B 5/7282* (2013.01); *A61B 5/7285* (2013.01)

(56) References Cited

U.S. PATENT DOCUMENTS

| | | | |
|---|---|---|---|
| 6,259,936 B1* | 7/2001 | Boggett | A61B 5/0261 600/310 |
| 6,616,613 B1 | 9/2003 | Goodman | |
| 6,676,608 B1 | 1/2004 | Keren | |
| 6,921,367 B2 | 7/2005 | Mills | |
| 2002/0188205 A1* | 12/2002 | Mills | 600/481 |
| 2006/0009700 A1* | 1/2006 | Brumfield | A61B 5/0261 600/504 |
| 2007/0287923 A1* | 12/2007 | Adkins et al. | 600/485 |
| 2009/0163969 A1* | 6/2009 | Donofrio | A61B 5/0084 607/6 |
| 2010/0001673 A1 | 1/2010 | Cardoletti | |
| 2011/0218448 A1* | 9/2011 | Buntic | A61B 5/0261 600/504 |
| 2011/0270050 A1* | 11/2011 | Naghavi et al. | 600/301 |

OTHER PUBLICATIONS

Swillens A et al., "Effect of an Abdominal Aortic Aneurysm on Wave Reflection in the Aorta", IEEE Transactions on Biomedical Engineering, IEEE Service Center, Piscataway, NJ, USA, vol. 55, No. 5, May 1, 2008 (May 1, 2008), pp. 1602-1611, XP011202567.

Shaltis, P. et al., "Calibration of the Photoplethysmogram to Arterial Blood Pressure: Capabilities and Limitations for Continuous Pressure Monitoring", Proceeding of the 2005 IEEE, Engineering in Medicine and Biology 27th Annual Conference, Shanghai, CN, Sep. 1-4, 2005, pp. 3970-3973.

Spigulis, J. et al., "Micro-Circulation of Skin Blood: Optical Monitoring by Advanced Photoplethysmography Techniques", Mar. 2009, University of Latvia, Physics Department and IAPS, Raina Blvd. 19, Riga, LV-1586, Latvia.

Kong Qinglong et al., "The Prevention of Complications After Interactivity Treatment of Infrarenal Abdominal Aortic Aneurysm", Chinese Journal of Surgery, v4, No. 7, Jul. 31, 2003.

Swillens, A. et al., "Experimental and Numerical Assessment of the Impact of Abdominal Aortic Aneurysms on Arterial Wave Reflection." Computer Methods in Biomechanics and Biomedical Engineering, Supplement 1, 2007, pp. 39-40.

\* cited by examiner

DETECTION AND MONITORING OF ABDOMINAL AORTIC ANEURYSM

FIELD OF THE INVENTION

The following pertains to the field of abdominal aortic aneurysm (AAA) and to non-invasive detection and monitoring of AAA, in particular.

BACKGROUND OF THE INVENTION

An abdominal aortic aneurysm is a pathological condition in which a part of the abdominal aorta becomes abnormally enlarged. This happens when a part of the aortic wall is weak. A ruptured aneurysm leads to severe internal bleeding and is, worldwide, a major cause of death. AAA develops slowly over years and most AAAs remain undiagnosed as this condition does not have specific symptoms. It is usually diagnosed when a person is screened, by ultrasound or CT scan for instance, for some other complaint. Once diagnosed, the patient has to be monitored periodically, say, every six months, using ultrasound or CT scans. Surgical intervention is prescribed when the aneurysm reaches a size at which there is a high risk of rupture. However, the patient cannot be monitored frequently enough to completely prevent a rupture as evidenced by the fact that a large number of ruptured AAAs occur in patients with previously diagnosed AAAs and are being monitored.

U.S. Pat. No. 6,921,367 B2 discloses a device for the diagnosis and management of peripheral vascular disease. It suggests that in addition to peripheral vascular disease, other diseases, such as abdominal aortic aneurysm, can be diagnosed and managed. It suggests further that changes in pulse wave velocity and waveform can be followed for years if desired. It describes a circuit schematic of the invention comprising a photoplethysmogram sensor. Two emitters and a detector are positioned adjacent the tissue being measured, such as a finger. In another embodiment, the photoplethysmogram sensor is combined with an ECG amplifier.

The article "Effect of an Abdominal Aortic Aneurysm on Wave Reflection in the Aorta" by Abigail Swillens et al., IEEE TRANSACTIONS ON BIOMEDICAL ENGINEERING, VOL. 55, NO. 5, MAY 2008, pp. 1602-1611, discloses that with AAA, pronounced reflections were present in the pressure and flow waveforms. Wave intensity analysis confirmed the presence of a backward expansion wave caused by sudden expansion of the aorta; this was absent without AAA. From a parameter study, it is clear that the impact of the AAA and the generation of the backward expansion wave augment with the increasing size of the AAA. The presence of AAA significantly alters wave reflection and hemodynamics in the aorta, with apparently measurable effects in humans. If this disturbance were measurable at easily accessible arteries, this might offer opportunities for assessing rupture risk and developing new noninvasive detection methods.

SUMMARY OF THE INVENTION

It is desirable to have a device and a method for detecting the presence of AAA in a subject non-invasively, without imaging and preferably in a general physician's clinic and without the need for a position sensor. Once AAA is diagnosed in a subject, by whichever means, it is preferable to monitor the subject non-invasively more frequently than possible hitherto. Further, it is preferable to estimate the progress of AAA in a non-invasive manner, once detected, without the need for the subject to visit a pathological facility or a hospital. It is more preferable to have a device and a method for monitoring the progress of AAA in the convenience of the subject's home. This would enable the subject to receive appropriate surgical intervention before the AAA ruptures. The invention is defined by the independent claims. The dependent claims define advantageous embodiments.

An embodiment provides a device for testing a subject for detecting a state of a vascular pathology of the subject, the device comprising a sensor signal unit for receiving a sensor signal representative of a blood volume in a body part of the subject, a comparator for comparing the sensor signal with a reference signal and a user interface for conveying a result based on the comparison to a user of the device.

A sensor that could be applied to a body part of a subject senses the volume of blood in the body part. The body part could be a finger, toe or earlobe of the subject, for instance. The volume of blood in any body part pulsates cardio synchronously, i.e., due to and in synchronism with the heartbeat of the subject. The sensor generates a signal representative of these pulsations in the blood volume in the body part. The signal is compared, after conversion to an electrical signal if necessary, with a reference signal. The reference signal could be a signal representative of the blood volume in a body part of a healthy individual, i.e., a person without AAA. The difference or differences between the sensor signal and the reference signal could then indicate the presence of AAA in the subject. Alternatively, the reference signal could be a sensor signal obtained from the subject soon after being diagnosed as having AAA, for instance by imaging means. The difference or differences between the sensor signal and the reference signal, in such a case, would indicate changes in the condition of AAA of the subject from the time of first diagnosis. A result of the comparison may be conveyed to the user of the device through the user interface. The result could be one or more of a set of indications that comprises at least a possible presence of AAA, a magnitude of change in AAA and a recommended action.

Thus the disclosed device may enable a general medical practitioner to detect a possible presence of AAA in a subject, without imaging, in a simple manner and without the need for a high level of expertise. It could also enable a lay person to monitor the state or progress of his or her AAA at home without having to periodically visit a hospital or a pathological facility. This may also reduce the possibility of a ruptured aneurysm during the longer interval between visits to a hospital or pathological facility which is the present practice.

Further, a method of detecting a state of a vascular pathology of a subject is disclosed herein. The method comprises a sensing step of sensing a blood volume in a body part of the subject and obtaining a sensor signal representative of the blood volume, a comparing step of comparing the sensor signal with a reference signal and a conveying step of conveying a result of the comparison to a user of the device.

By comparing the sensor signal with a reference signal, the method enables the detection of a possible presence of AAA in a subject or an estimation of a progress of the state of pathology. By comparing the signal with a reference signal from a healthy subject the possible presence of AAA could be detected. However, ascertaining the exact nature, location and condition of the AAA may require the application of imaging modalities such as ultrasound or CT or MRI. By comparison of the sensor signal with the reference signal previously acquired from the subject, the method enables the estimation of the progress of AAA either from the time of first diagnosis, at which time the reference signal was acquired or from any instance earlier than the current test when the signal was acquired and stored as a reference signal.

These and other aspects will be described in detail hereinafter, by way of example, on the basis of the following embodiments and implementations.

Figure 1:
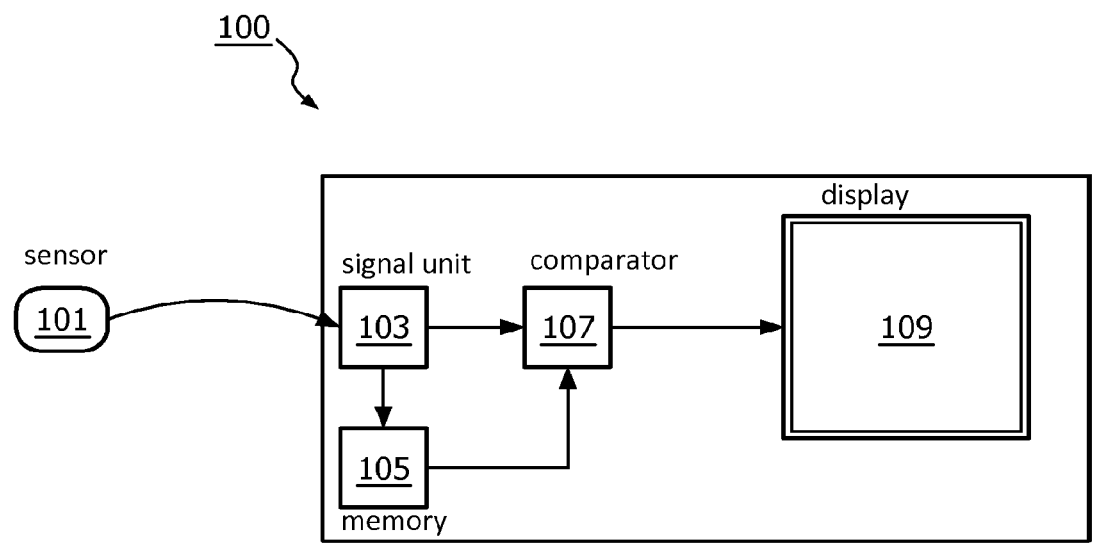
FIG. 1 is a schematic diagram of an embodiment of the disclosed device.

A common reference numeral in different figures refers to the same element in all the different figures.

DETAILED DESCRIPTION OF EMBODIMENTS

FIG. 1 shows a schematic representation of an embodiment of the disclosed device, shown generally as 100. During the use of the device on a subject a sensor 101 is applied to a body part of the subject, in a removable manner. The sensor 101 senses the blood volume in the body part to which it is applied and produces a signal representative of the blood volume in the body part. Because of the heartbeats of the subject the blood volume pulsates through all body parts. Thus, the signal from the sensor 101 has a pulsating waveform, in synchronism with the heartbeat of the subject. Further, the waveform has a dc component or an essentially constant component that is due to the minimum amount of blood that stays in the body part.

The sensor signal unit 103 processes and analyses this sensor signal for comparison with a reference signal stored in the memory unit 105. It is also possible that the reference signal is stored in an external memory device and is accessible by the disclosed device. The sensor signal may be analog amplified and filtered before it is digitized. Once digitized it may be stored in a temporary memory (not shown) or in the memory unit 105 for further analysis and comparison. Any of the known waveform analysis methods could be used for the analysis. For instance, the signal may be analyzed by Fourier analysis and a spectrum of the signal obtained. This spectrum may be compared in a comparator 107 with the spectrum of the reference signal, to obtain the differences between the two signals.

The results of the comparison are displayed in a suitable manner on the display 109. A result of the comparison could be the possible presence of AAA in the subject. The results could also be displayed in terms of the actions to be taken by the user or the subject. It is to be understood that the subject could also be the user. The reference signal and the signal acquired during the use of the device on a subject could be displayed as waveforms, as in a digital oscilloscope, for instance, for visual comparison. The display could be a combination of the methods described above.

Alternatively, the signals could be compared in a time domain analysis. In this method of analysis and comparison, the characteristics of the sensor signal are compared with the corresponding characteristics of the reference signal to determine the differences between the two.

A suitable sensor for sensing the pulsations of blood volume is a photoplethysmogram sensor (PPG sensor), for example. A PPG sensor may be either of transmission type or reflective type. In the former case the PPG sensor radiates light into a body part at a first side of the body part and collects the light transmitted through the body part, at the opposite side of it. The characteristics of the light are altered when it passes through the blood in the body part. The magnitude of the change depends on the volume of blood in the body part and hence the signal from the PPG sensor is representative of the blood volume in the body part. In the latter case the light reflected by the body part is collected and a signal proportional to the collected light is generated which is representative of the blood volume in the body part. As the pulse wave observed in the PPG sensor signal reflects the pressure wave, the changes caused to the pressure wave by AAA can be observed in the PPG sensor signal.

Other sensors based on impedance measurement or strain gauges which measure the peripheral blood pressure could also be used.

Convenient locations for the attachment of the sensor are the earlobe, the forefinger or any other finger of the subject, one of the toes, the ankle or forehead. When a PPG sensor is used, except in the last two body parts mentioned, a transmission type of PPG sensor could be used with advantage. In the case of the last two a reflection type PPG sensor could be used.

The PPG sensor signal is normally ac-coupled to the signal processing circuitry to block the dc component of the signal. However, for use with the disclosed device it may be advantageous to dc-couple the PPG sensor signal and derive useful information from the dc signal also. For instance, a large or increasing dc value may indicate that the aneurysm is enlarging, thereby reducing the perfusion of the body part to which the PPG sensor has been attached. Similar advantages may be realized by dc-coupling other types of sensors mentioned as well.

Figure 2:
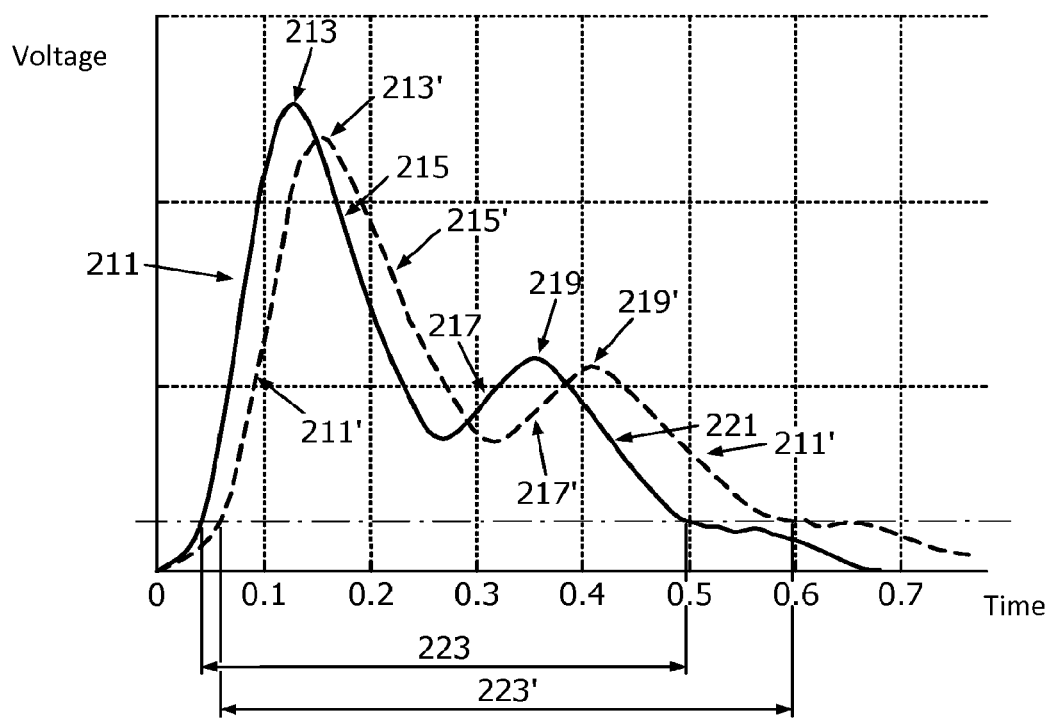
FIG. 2 is an exemplary representation of a signal representative of the blood volume in a body part of a subject and a reference signal.

FIG. 2 shows exemplarily the blood volume signals obtained by a PPG sensor from a normal subject with a continuous line and the one acquired from a subject with AAA with a broken line. Some of the different parts of the reference signal are exemplarily identified with reference numerals and the corresponding parts of the sensor signal obtained from a subject with AAA are identified with corresponding reference numerals with apostrophes.

The characteristics of the two signals that could be compared to determine the differences are the slopes of the rising edges 211 and 211', 217 and 217' of the two signals, the peak voltages 213 and 213', 219 and 219', the slopes of the falling edges 215 and 215', 221 and 221', for example. Further characteristics of the waveforms such as the pulse widths 223 and 223' of the two signals, as measured with reference to a predetermined dc level and the time difference between the occurrences of corresponding peaks, for example, could also be used for comparison. A person skilled in the art may recognize characteristics other than those mentioned that offer themselves for comparison for drawing useful conclusions. Still further, the derivative of the sensor signal may be obtained and compared with the derivative of the reference signal in a similar fashion, to obtain useful information.

Even though in FIG. 2, the sensor signal and reference signals obtained from a PPG sensor is shown exemplarily, sensor signals from any other sensor type mentioned earlier will have a similar wave shape and differences between the reference signal from a normal individual and the sensor signal from a subject with a vascular pathology.

Once the sensor signal has been compared with the reference signal and the differences between the two are obtained, they are used to assess one or more of the possible presence of AAA in a subject, the progress of AAA and the rate of progress of AAA depending on the signal used as the reference signal and decisions could be drawn from them. These decisions and other relevant details and recommendations may be conveyed through a suitable user interface 109 for the information of the subject or the user. The user may be a doctor or a care giver or the subject, for instance.

The device is particularly useful for detecting the possible presence of AAA. If the device detects a possible presence of AAA, the subject may be recommended to undergo further tests, especially using imaging modalities such as CT, Ultrasound or MRI, to confirm the presence of AAA and to determine its exact location in the abdomen and the size of the aneurysm. The device is also useful for monitoring the state and progress of AAA once AAA has been detected and confirmed. The subject may use the device at home and avoid periodic visits to the doctor or hospital or a pathological facility which may be inconvenient and expensive. As described before, the interval between such visits, say every six months, may be too long to prevent a possibility of a ruptured aneurysm. With the subject testing himself or herself much more frequently, for example every fortnight, using the disclosed device, it is likely to prevent unanticipated ruptures and the patient may be recommended to undergo surgical intervention well before a rupture is likely to occur.

The reference signal may be stored in the memory 105, after suitable signal processing and digitizing. The reference signal may be obtained from a single healthy subject by using the disclosed device. That is to say that the device is used to acquire the signal but, not used for any comparison in this case. Alternatively, it may be obtained from a number of healthy subjects and an average or representative signal may be synthesized. However, there may be significant differences between signals from healthy subjects, depending on factors such as age and sex. Thus it may be necessary to obtain a number of such reference signals and an appropriate signal from the group of stored signals may be used as reference, while using the device on a subject.

Alternatively, the reference signal may be obtained from the subject once AAA has been diagnosed in the subject by the use of the disclosed device or by other means. All comparisons may be with this reference signal as described hitherto. Alternatively, the signal acquired each time the device is used on the subject may be stored and used as the reference signal for the subsequent use of the device on the same subject. This may have the disadvantage that the differences between the reference signal and the acquired signal could turn out to be too small to make conclusive decisions. In that case, the signal acquired and stored during the first use of the device on the subject may be used as the reference signal. Alternatively if the differences are too small to provide any useful information, the signal may be stored in the memory 105 for future use, declaring that there has been no or negligible change or progress in AAA.

The signal obtained from the sensor is different for different body parts of the same subject. Hence, the body part selected for each subsequent use of the device on a subject is maintained the same. Alternatively, to obtain the maximum possible information about the progress of AAA, the sensor could be attached to different body parts, signals obtained therefrom and compared with the reference signals which have also been acquired from the same body parts and stored. This is likely to enhance the reliability of the tests.

Thus, the choice of the reference signal for comparison may be determined at least based on age, sex and the body part from which the signal has been acquired.

The device may be used by a general physician to screen subjects for AAA and recommend further confirmatory tests with imaging modalities in case a possible presence of AAA is indicated by the device. The confirmatory tests may also assess the state and location of the AAA in the subject. The subject could then use the disclosed device in the convenience of his or her home to monitor himself or herself and consult a specialist only when needed. The device may also be configured to recommend to the subject to consult a specialist. The intervals between tests may be determined by the physician at the time of the first use of the device on the subject and recommended to the subject. The subject will then carry out the tests and take actions based on the results. It is also possible that in case the progress of AAA is higher than during the previous intervals, the intervals between tests could be reduced and recommended to the subject by the physician.

It is to be understood that even though the sensor signal is described hitherto in the singular, the device may acquire a predetermined number of pulses of adequate quality before it compares each of them with the reference signal. This is necessitated by the fact that the quality of the sensor signal could be affected by factors such as subject movement, improper position of the subject, improper application of the sensor to the body part, etc., to name a few.

Factors such as the relative positions between the thorax and the body part to which the sensor is applied and the posture of the subject during the acquisition of the sensor signal may influence the wave shape of the signal. Thus, care has to be exercised when a physician recommends the use of the disclosed device to a subject diagnosed with AAA and acquires reference signals from the subject for future use. The physician could record the posture of the subject when the reference signals are being acquired and recommend that the subject assume the same posture while using the device in future. The same precautions are to be taken while acquiring the reference signals from healthy subjects for storing as reference signals for detecting AAA.

It is to be understood further that the sensor signal need not be an electrical signal when it leaves the sensor. It could be an optical signal conveyed to the device through fiber optic cables. The signal may then be converted to an electrical signal in the device. This may also reduce noise in the signal as the optical signal is immune to electromagnetic noise.

It is to be understood that even though the sensor has been described as a part of the disclosed device, the sensor could be detachably connected to the device. Further, this feature may be advantageous since the use of the transmission type and reflective type of PPG sensors may be employed, as required, to make the tests on a subject more reliable. Alternatively, sensors of other known types could also be used by detachably connecting them to the device.

Figure 3:
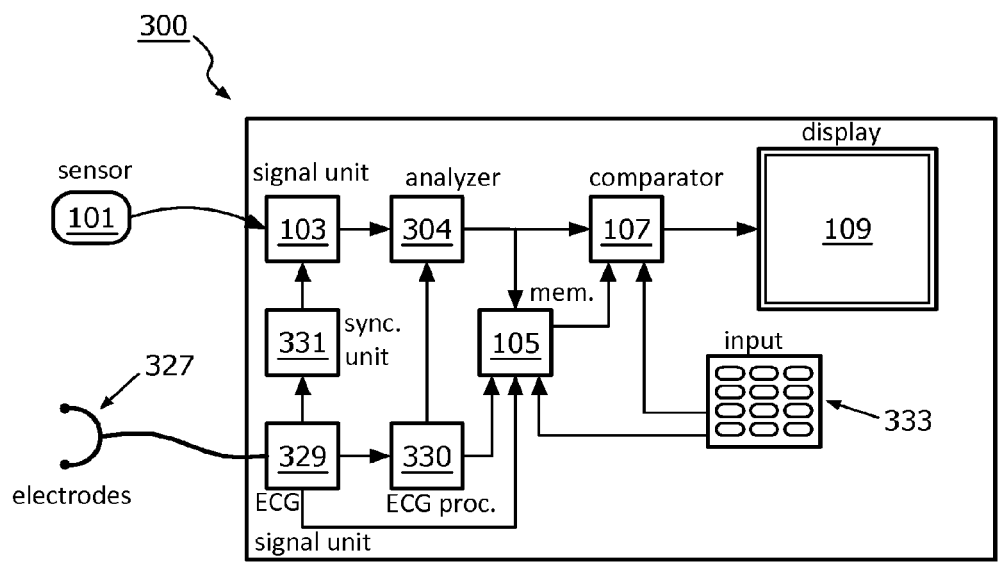
FIG. 3 is a schematic diagram of another embodiment of the disclosed device wherein the electrocardiogram signal of the subject is also acquired.

FIG. 3 schematically represents another embodiment of the disclosed device, shown generally as 300. In this embodiment, the device includes an electrocardiogram (ECG) signal unit 329 for acquiring an ECG signal of the subject and a synchronizer 331 for synchronizing the acquisition of the sensor signal representative of the blood volume by sensor signal unit 103, with the ECG signal. The ECG signal is used for a robust feature extraction from the sensor signal by the use of the timing of the peak of the ECG signal. The pulse rate and the time interval between the ECG signal and the sensor signal varies from person to person and in the same person, from time to time. The time interval between the peak of the ECG signal and the sensor signal is analyzed for a number of cycles before using it for the robust feature extraction.

Further, the ECG signal processing unit 330 processes the ECG signal of the subject and the signal analyzer unit 304 processes the sensor signal based on the ECG signal. The phase relationship between the ECG signal and the sensor signal may also be used to assist the comparison of signals. Further, a change in the phase relationship between the ECG signal and the sensor signal could also reveal the presence of AAA along with other results of the comparison and similarly reveal the progress of AAA in the subject.

In a device according to this embodiment, when the reference signals are being acquired, they too could be acquired using the timing information provided by the ECG signal. During a test, the sensor signal could be compared with the reference signal with the ECG signal providing the timing information for the comparison.

It is to be noted that the heart rate of the subject at the time of acquisition of a sensor signal for a test is most likely to be different from the heart rate of the subject during the previous test or that of a healthy person chosen to provide the reference signal at the time of acquiring the reference signal. The acquisition of the ECG signal helps in compensating for the differences in heart rates while comparing the sensor signal with the reference signal.

The ECG electrodes 327 may be a part of the disclosed device. However, it is not essential that they are a part of the disclosed device and the electrodes are only plugged into the device when needed. They may also form a part of wearable electronic devices or electrodes integrated in textiles and it is sufficient that the ECG signal is conveyed to the disclosed device for processing.

Further, the disclosed device could have an input means 333, a keypad for instance, for user inputs to be entered into the device. The user could enter the information such as the body part to which the sensor is attached, age and sex of the subject, whether reference data is being acquired for storing or a test being conducted with the device and such information. The user interface is shown exemplarily and the actual design may take many different forms.

Figure 4:
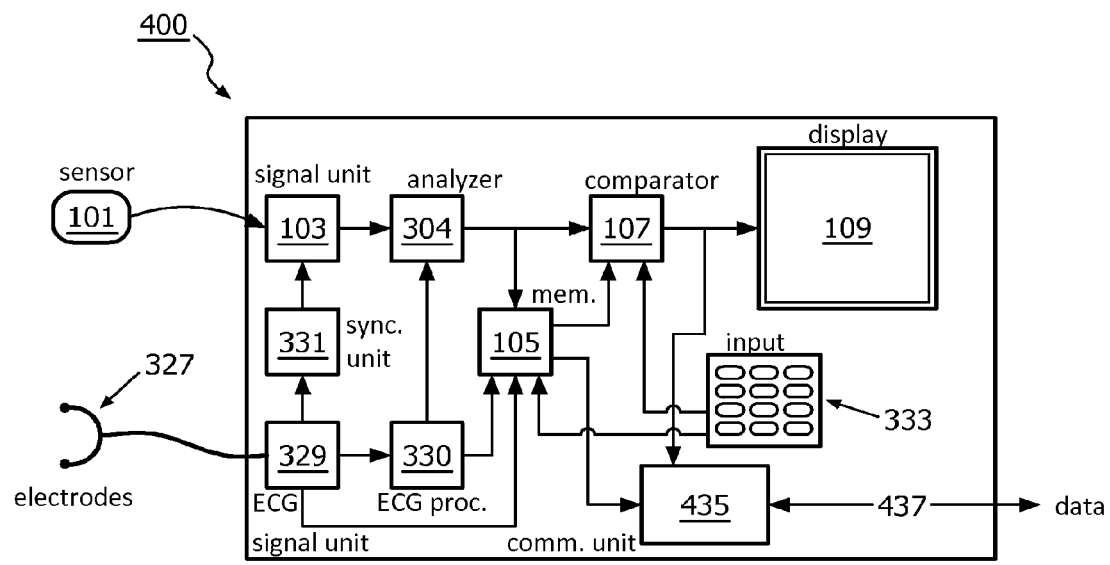
FIG. 4 is a schematic diagram of one more embodiment of the disclosed device with a communication means for communicating data with an external device.

FIG. 4 is a schematic diagram of another embodiment of the disclosed device, shown generally as 400, comprising a bidirectional communication unit 435. This unit 435 can communicate data 437 that could be the acquired sensor signals or the results of the tests or both to a remote location, for instance a device that could be used by a doctor or another medical specialist. This communication may take place in a wired or wireless manner, using known wireless or wired communication protocols for instance. With this, the subject's physician has access to the subject's test data and the results of the comparison, wherever the test is conducted, and can make decisions regarding the tests and the progress of AAA of the subject. The physician or another specialist could take decisions based on the results of the tests. The decisions could be conveyed to the subject to change the interval between the tests in future or to see a specialist for further tests and such. These could be received by the bidirectional communication device 435 and displayed to the subject.

It is to be understood that even though the acquisition and processing of the sensor signal and the ECG signal and the comparison with the reference signal and conveying the result to the user are described as if they occur essentially in real-time, it is not necessarily so. Since it may be essential to obtain a number of cycles of the sensor signal and compare them with the reference signal, the acquisition of the sensor signal and the ECG signal is carried out in real time and the rest of the functions are carried out at a later time.

Figure 5:
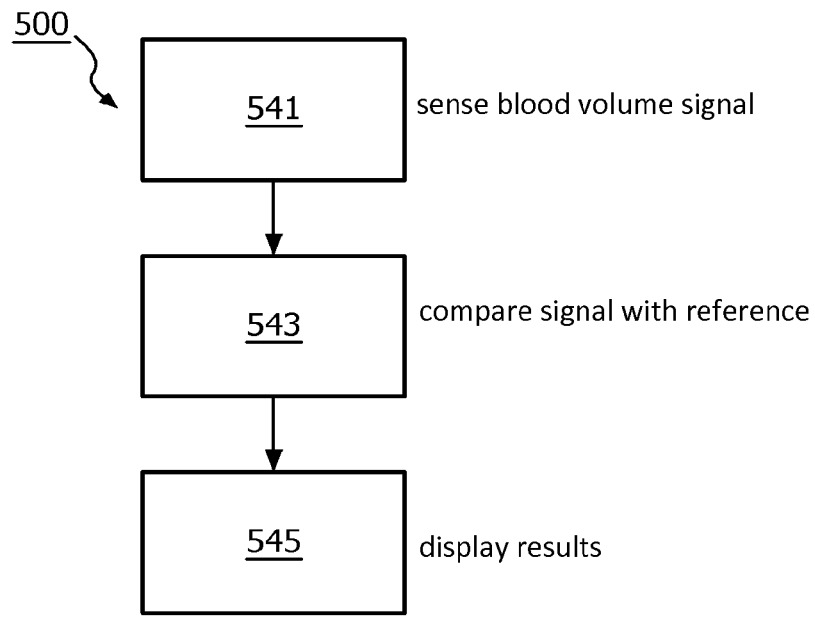
FIG. 5 is a schematic diagram of a disclosed method for non-invasively detecting a state of AAA of a subject.

FIG. 5 shows diagrammatically, a method, shown generally as 500, of detecting a state of a vascular pathology of a subject. The method comprises a sensing step 541 of sensing a blood volume in a body part of a subject and obtaining a signal representative of the blood volume, a comparison step 543 of comparing the signal with a reference signal and a conveying step 545 of conveying a result of the comparison to a user of the device. In the sensing step 541 the blood volume in a body part of a subject is sensed externally or non-invasively. A suitable sensor for doing this is a PPG sensor. Other sensors based on impedance measurement or strain gauges which measure the peripheral blood pressure may also be suitable. The sensor may be applied to a body part of a subject and a signal representative of the blood volume in the body part could be obtained. This signal pulsates in synchronism with the heartbeats of the subject. The signal is compared with a reference signal in a comparison step 543. The reference signal may be stored in a suitable memory unit.

Figure 6:
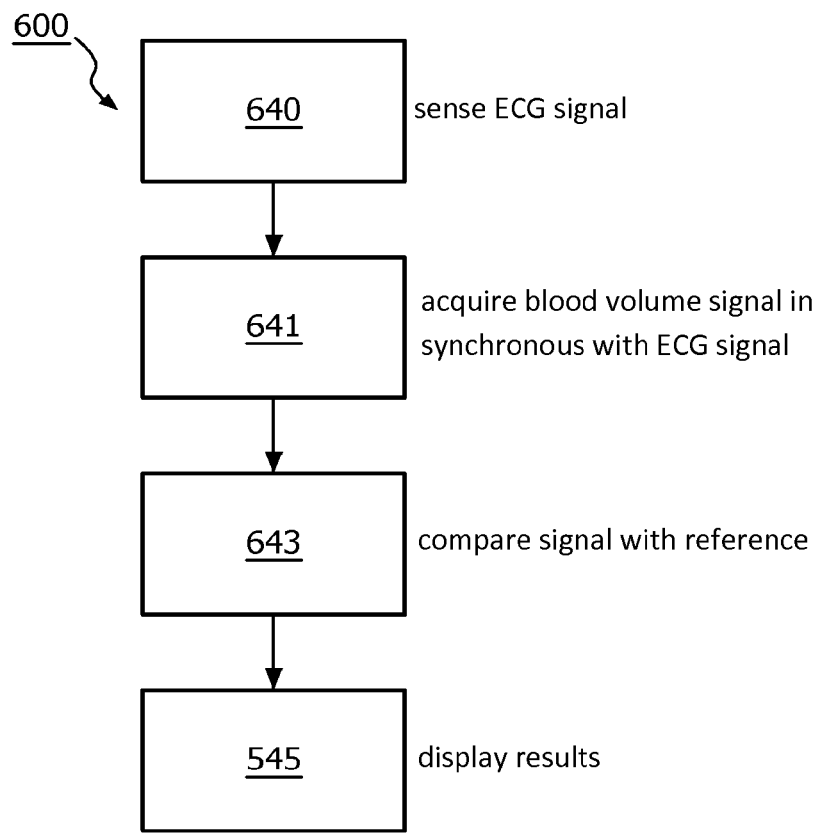
FIG. 6 is a schematic diagram of another disclosed method for non-invasively detecting a state of AAA of a subject, including acquiring an electrocardiogram signal of the subject.

FIG. 6 shows a further method, shown generally as 600, that includes a sensing step 640 of sensing an electrocardiogram signal of the subject, a synchronized acquisition step 641 of synchronizing an acquisition of the signal representative of the blood volume with the electrocardiogram signal and a comparison step 643 of comparing the signal representative of the blood volume with a reference signal, depending on the electrocardiogram signal. The results of the comparison with the reference signal or a result based on the comparison or both are displayed suitably in a display step of 545.

The heartbeat is triggered by electrical activity of the heart muscle and the electrical activity is sensed as the ECG signal. Thus, if the electrical activity is sensed, it gives a prior indication of the activity of the heart muscle that follows. Depending on the body part on which the sensor is applied, the signal representative of the blood volume in the body part rises after a definite time delay with reference to the ECG signal indicating the systolic action of the heart, for instance. Thus the ECG signal could be used to acquire the signal representative of the blood volume more robustly when the signal acquisition is synchronized with the ECG signal. For instance, during the rest period between heartbeats, the dc component in the sensor signal could be sensed and amplified with a higher amplification. Once the ECG signal indicates systolic action and indicates that the blood volume would rise due to the heartbeat, the gain for the sensor signal representative of the blood volume could be reduced. Similarly the filter coefficients of a filter used for filtering the sensor signal could be changed based on the ECG signal to acquire the signal with optimum parameters. This type of signal acquisition could lead to more robust signals and render the comparison with the reference signal more reliable.

Further, the comparison of the sensor signal with the reference signal could also be referenced to the ECG signal. Since the heart rate of the subject at the time of acquiring the signal representative of the blood volume is most likely to be different from the heart rate at the time of acquisition of the reference signal, the comparison of the two signals would be difficult. However, with the acquisition of the ECG signal while acquiring both the test signal and the reference signal, the time period of one of the signals could be contracted or dilated to match with the other. This compensates for the differences between the timing of the two signals and makes the comparison of the signals normalized in time.

While the embodiments have been described in detail in the drawings and description, such drawings and description are to be considered exemplary and not restrictive; the invention is not limited to the disclosed embodiments.

For example, it is possible to practice the invention in an arrangement wherein there are more than one computer memory units to store the various signals. While the sensor signals are being acquired, they may be stored in a temporary volatile memory and after the processing and comparison they may be stored in a non-volatile memory. Similarly, the steps of methods disclosed in different embodiments may be combined with advantage. For instance the ECG signal may be used only in the comparison step, with advantage, and not used in the sensor signal acquisition step. Further variations and combinations will occur to a practitioner and all such variations are deemed to be within the scope of the disclosed methods.

Other variations to the disclosed embodiments can be understood and effected by those skilled in the art, in practicing the claimed invention, from a study of the drawings, the disclosure, and the appended claims. In the claims, the word "comprising" does not exclude elements or steps other than those mentioned, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

The invention claimed is:

1. A device for testing a subject for estimating a progress of a state of an existing abdominal aorta aneurysm of the subject based on a determined change over time, the device comprising:
    a sensor configured to sense a pulsation of blood volume in a body part of the subject;
    a memory;
    a processor configured to:
        acquire from the sensor an amplified sensor signal representative of the blood volume in the body part of the subject;
        acquire an electrocardiogram (ECG) signal of the subject via an ECG electrode, the ECG signal indicating an activity of the heart muscle of the subject;
        analyze a time interval between a peak of the ECG signal and the sensor signal for a number of cycles so as to synchronize the acquisition of the sensor signal with the ECG signal;
        increase the amplification of a DC component of the sensor signal to a higher amplification for the time period when the ECG signal indicates that the heart muscle of the subject is in a diastolic state, and reduce the amplification of the DC component of the sensor signal for the time period when the ECG signal indicates that the heart muscle of the subject is in a systolic state;
        compare one or more characteristics of the sensor signal with corresponding one or more characteristics of a reference signal stored in the memory, wherein the reference signal is a corresponding sensor signal previously acquired from a test on the subject a time period ago, timing information of the ECG signal being used to compensate for a difference in heart rates of the subject between acquisitions of the sensor signal and the reference signal; and
        determine a change in the one or more characteristics of the sensor signal over the time period; and
    a user interface configured to display a result of the determination,
        wherein the result provides an estimate of the progress of the state of the existing abdominal aorta aneurysm.

2. The device of claim 1, wherein the sensor is a photoplethysmogram sensor.

3. The device of claim 1, wherein the processor is further configured to:
    determine a change in one or more relationships between the sensor signal and the ECG signal of the subject,
    wherein the one or more relationships comprise the time interval between a peak of the ECG signal and the sensor signal,
    and further wherein the result of the determination is based upon the determined change in the one or more relationships between the sensor signal and the ECG signal.

4. A method of testing a subject for estimating a progress of a state of an existing abdominal aorta aneurysm of the subject based on a determined change over time, the method comprising:
    sensing a pulsation of blood volume in a body part of the subject with a sensor and acquiring an amplified sensor signal representative of the blood volume;
    acquiring, by a processor, an electrocardiogram (ECG) signal of the subject via an ECG electrode, the ECG signal indicating an activity of the heart muscle of the subject;
    analyzing, by the processor, a time interval between a peak of the ECG signal and the sensor signal for a number of cycles so as to synchronize, by the processor, the acquisition of the sensor signal with the ECG signal;
    amplifying to a higher amplification, by the processor, a DC component of the sensor signal when the ECG signal indicates that the heart muscle of the subject is in a diastolic state, and reducing the amplification of the DC component of the sensor signal for the time period when the ECG signal indicates that the heart muscle of the subject is in a systolic state;
    comparing, by the processor, one or more characteristics of the sensor signal with corresponding one or more characteristics of a reference signal stored in a memory, wherein the reference signal is a corresponding sensor signal previously acquired from a test on the subject a time period ago, timing information of the ECG signal being used to compensate for a difference in heart rates of the subject between acquisitions of the sensor signal and the reference signal;
    determining, by the processor, a change in the one or more characteristics of the sensor signal over the time period; and displaying a result of the determination, wherein the result provides an estimate of the progress of the state of the existing abdominal aorta aneurysm.

5. The method of claim 4, further comprising determining a change in one or more relationships between the sensor signal and the ECG signal,
wherein the one or more relationships comprise the time interval between a peak of the ECG signal and the sensor signal,
and further wherein the result of the determination is based upon the determined change in the one or more relationships between the sensor signal and the ECG signal.

* * * * *